US007938792B2

(12) United States Patent
Roger et al.

(10) Patent No.: US 7,938,792 B2
(45) Date of Patent: May 10, 2011

(54) ADAPTIVE ALGORITHM FOR ACCESS DISCONNECT DETECTION

(75) Inventors: Rodolfo G. Roger, Clearwater, FL (US); Michael E. Hogard, Odessa, FL (US); Joel Tejedor, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 768 days.

(21) Appl. No.: 11/865,531

(22) Filed: Oct. 1, 2007

(65) Prior Publication Data

US 2009/0088683 A1 Apr. 2, 2009

(51) Int. Cl.
*A61M 37/00* (2006.01)
*C02F 1/44* (2006.01)
*G01F 1/20* (2006.01)

(52) U.S. Cl. ............ 604/6.09; 604/5.04; 604/6.08; 604/6.11; 210/645; 210/739; 73/861.18

(58) Field of Classification Search .......... 210/645–646, 210/739; 604/5.04, 6.08, 6.09–6.11, 6.05, 604/6.06, 6.16, 264, 43, 65–67; 73/861.02, 73/861.08, 861.12
See application file for complete search history.

(56) References Cited

U.S. PATENT DOCUMENTS

| | | | |
|---|---|---|---|
| 5,242,434 A | 9/1993 | Terry | |
| 5,744,027 A | 4/1998 | Connell et al. | |
| 6,143,181 A | 11/2000 | Falkvall et al. | |
| 6,796,955 B2 | 9/2004 | O'Mahony et al. | |
| 7,040,142 B2 | 5/2006 | Burbank | |
| 7,115,228 B2 | 10/2006 | Lundtveit et al. | |
| 7,153,286 B2 | 12/2006 | Busby et al. | |
| 7,172,570 B2 | 2/2007 | Cavalcanti et al. | |
| 7,264,730 B2 | 9/2007 | Connell et al. | |
| 7,303,680 B2 | 12/2007 | Connell et al. | |
| 2003/0194894 A1* | 10/2003 | Wariar et al. | 439/191 |
| 2003/0195454 A1 | 10/2003 | Wariar et al. | |
| 2005/0131331 A1* | 6/2005 | Kelly et al. | 604/4.01 |
| 2007/0112289 A1 | 5/2007 | Cavalcanti et al. | |
| 2008/0065006 A1 | 3/2008 | Roger | |
| 2008/0195021 A1 | 8/2008 | Roger | |

(Continued)

FOREIGN PATENT DOCUMENTS

EP 1110566 6/2001

OTHER PUBLICATIONS

International Search Report and the Written Opinion for International Application No. PCT/US2008/067368 mailed on Feb. 19, 2009.

*Primary Examiner* — Leslie R Deak
(74) *Attorney, Agent, or Firm* — K&L Gates LLP

(57) ABSTRACT

An extracorporeal therapy machine removes blood from a patient in order to treat the blood and then return the blood to the patient. If the removal needle or the return needle is dislodged and blood is not returned, the patient may suffer a great blood loss. A new technique for detecting dislodgement uses the normal, initial values of a plurality of parameters of the patient and the therapy machine to set criteria or limits for an alarm, and then adjusts those criteria based on the later values of those parameters as they change during one therapy or over several therapies experienced by the patient.

23 Claims, 10 Drawing Sheets

U.S. PATENT DOCUMENTS

| | | |
|---|---|---|
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0105627 A1 | 4/2009 | Rohde |
| 2010/0022934 A1 | 1/2010 | Hogard |
| 2010/0022935 A1 | 1/2010 | Muller |

* cited by examiner

ADAPTIVE ALGORITHM FOR ACCESS DISCONNECT DETECTION

BACKGROUND

The invention is in the field of medical treatments generally and patient vascular access systems. The present invention relates to embodiments for detecting blood leakage during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421. There are also other related procedures, such as hemofiltration or hemodiafiltration in which needle dislodgement should be avoided in order to safeguard the health of the patient.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery or an arteriovenous fistula/graft, and a needle and a pump are used to provide the blood to the therapeutic machine. It is relatively simple to detect a problem withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

One embodiment is a method for detecting an access disconnection. The method includes steps of inputting or accessing information about a patient for an extracorporeal blood therapy, inputting or accessing at least one value for an alert criterion for an access disconnection, beginning the extracorporeal blood therapy, taking a first reading of a plurality of properties concerning the therapy and blood of the patient, proceeding with the extracorporeal blood therapy, taking a second reading of the plurality of properties concerning the therapy and the blood of the patient, calculating a change in the at least one value for the alert criterion based on the second reading of the plurality of properties, and adjusting the at least one value for an alert for the access disconnect criterion.

Another embodiment is a method for detecting an access disconnection. The method includes steps of inputting or accessing information about a patient for an extracorporeal blood therapy, selecting or accessing at least one electrical property value of an electrical circuit selected from the group consisting of the patient and an extracorporeal blood therapy machine as an alert criterion for an access disconnection, beginning the extracorporeal blood therapy, taking a first reading of a plurality of properties concerning the therapy and blood of the patient, proceeding with the extracorporeal blood therapy, taking a second reading of the plurality of properties concerning the therapy and the blood of the patient, calculating a change in the electrical property value of the alert criterion based on at least one change in the plurality of properties, and adjusting the alert criterion value.

Another embodiment is an access disconnect detection system The system includes arterial and venous contacts configured for use with an extracorporeal blood therapy machine for administering a therapy, an electrical circuit connected to the contacts, the electrical circuit configured for sensing at least one electrical property sensed by the contacts, at least one sensor configured for sensing a property concerning the patient or a component of the extracorporeal blood therapy machine, a computer having a memory, the computer configured for receiving and storing values for a plurality of properties concerning the patient and the extracorporeal blood therapy machine, and a computer program on a computer readable medium configured for accepting first values of the plurality of properties, and for using or setting an initial criterion for determining an access disconnection, and for accepting second values of the plurality of properties and for adjusting the criterion based on the second values.

Another embodiment is an extracorporeal therapy machine for administering a dialysis therapy. The extracorporeal therapy machine includes arterial and venous contacts configured for use with the machine, an electrical circuit connected to the contacts, the electrical circuit configured for sensing an electrical property concerning the patient or a component of the machine, a computer having a memory, the computer configured for receiving and storing values for a plurality of properties concerning the patient, the therapy, and the machine, a computer program on a computer readable medium configured for accepting first values of the plurality of properties, and for setting an initial criterion for determining an access disconnection, and for accepting second values of the plurality of properties and for adjusting the criterion based on the second values, and at least one input device and one output device operably connected to the computer.

Another embodiment is a hemodialysis machine for administering a hemodialysis therapy. The hemodialysis includes a housing containing components of the machine, a monitor for monitoring the machine, a dialyzer, at least one blood pump for moving blood of the patient to and from the patient and through the dialyzer, arterial and venous contacts configured for use with the machine, an electrical circuit connected to the contacts, the electrical circuit configured for sensing an electrical property concerning the patient or a component of the machine, a computer having a memory, the computer configured controlling the machine and for receiving and storing values of a plurality of properties concerning the patient, the therapy, and the machine, a computer program on a computer readable medium configured for accepting first values of the plurality of properties, and for setting an initial value for a criterion for determining an access disconnection, and for accepting second values of the plurality of properties and adjusting the criterion value based on the second values; and at least one input device and one output device operably connected to the computer.

Additional features and advantages are described herein, and will be apparent from, the following Detailed Description and the figures.

DETAILED DESCRIPTION

Figure 1:
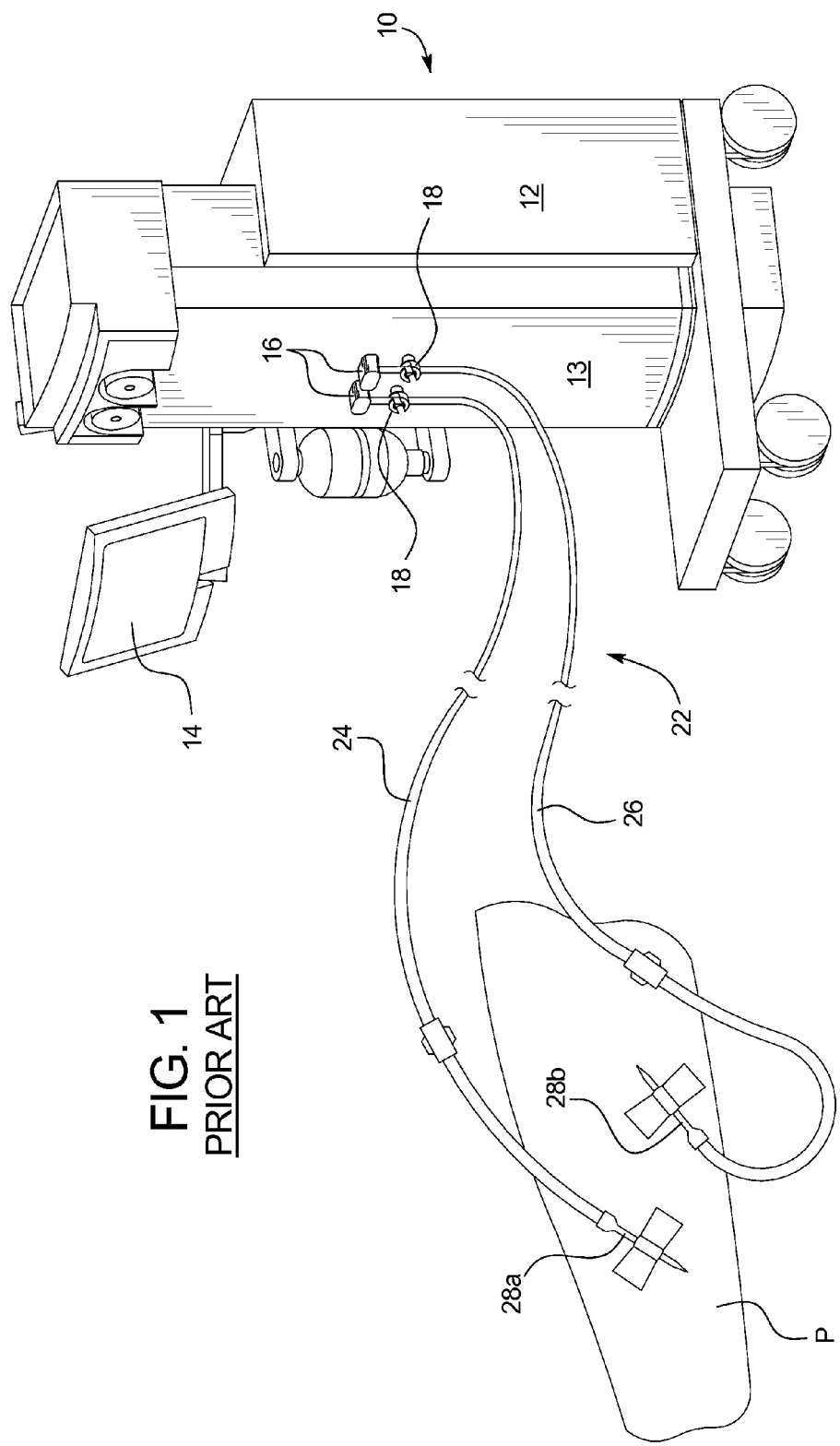
FIG. 1 is perspective view of a prior art hemodialysis machine connected to a patient for an extracorporeal blood therapy treatment.

Access connection may be monitored in many ways. One method is to have a caregiver, such as a nurse or a home aide, supervise the procedure. This is impractical for several reasons, including at least expense and patient comfort. Therefore, as noted above, several methods have been devised to monitor access sites using sensors. One method to monitor access connection is to measure the electrical properties between sections of the arterial and venous lines connected to the patient. In case of an access disconnection, the electrical properties will change dramatically. For example, conductivity will go to a very low value and impedance will rise quickly.

There are several factors that affect the value of the conductivity and the impedance. The blood of each patient has particular chemical characteristics that affect its conductivity. These characteristics evolve through the period for therapy as the blood chemistry and hematocrit concentration changes. The section of the extracorporeal circuit that includes the blood pump, the drip chamber or chambers and the dialyzer constitute another impedance that is in parallel with the patient connection. This impedance changes as the blood pump rotates and generates different levels of occlusion. The impedance also changes with blood pump speed, with dialysate flow and concentration, and with the infusion of medication, such as infusion of a drug or a bolus of heparin or saline, into the blood stream, as part of a therapy. Each of these parameters has an influence on the electrical impedance measured by the access monitor system.

An Extracorporeal Therapy Machine

The present disclosure can include any suitable dialysis machine for such purposes. An example, of a hemodialysis machine of the present disclosure is disclosed in U.S. Pat. No. 6,143,181 herein incorporated by reference. Also incorporated by reference is U.S. patent application Ser. No. 11/676,110, entitled Enhanced Signal Detection for Access Disconnection Systems, assigned to the assignee of the present patent. In one embodiment, the dialysis machine 10 includes a mobile housing 12 and it has at the front side 13 thereof connectors 16 for connecting tubing or the like by which a patient can be connected to the dialysis machine. A flat touchscreen monitor 14, which can show several operational parameters, is provided with symbols and fields for adjustment of the dialysis machine. Monitor 14 can be adjusted vertically and can be universally pivoted relative to housing 12 of dialysis machine 10 and can be fixed in the desired adjusted position. Other input devices may for a dialysis machine include a keyboard, a keypad, a mouse, a disc drive and a wired or wireless connection to computer network, such as a hospital information system, a clinic information system, the Internet, or other outside connection. Other output devices include a local speaker or a printer for the hearing impaired.

In an embodiment, dialysis machine 10 includes a housing or chassis 12 having one or more connectors for connecting a patient to the dialysis machine via a blood circuit allowing blood to flow between the patient and the dialysis machine during dialysis therapy, wherein one or more electrical contact is connected to the blood circuit in fluid communication with the blood allowing detection of a change in an electrical value in response to access disconnection as the blood flows through the blood circuit having an electrical signal passing therein.

In one embodiment, dialysis machine 10 can be designed to accommodate one or more of the electrical contact coupling devices, such as a pair of coupling devices, used to detect access disconnection as shown in FIG. 1. For example, one or more coupling devices 18 can be attached to the front side 13 of the dialysis machine 10. This can be done in any suitable way. In one embodiment, a stem portion of the coupling device is insertably mounted via a threaded fit, frictional fit or the like. This connects the patient to the dialysis machine 10 via a blood tubing set 22. The blood tubing set includes a first blood line 24 and a second blood line 26. In an embodiment, the first blood line 24 is connected to the patient via an arterial needle 28a or the like through which blood can flow from the patient 20 to the dialysis machine 10. The second blood line 26 is then connected to the patient 20 via a venous needle 28b or the like through which fluid flows from the dialysis machine to the patient to define a blood circuit.

Alternatively, the first blood line and the second blood line can be coupled to the venous needle and the arterial needle, respectively. The blood lines are made from any suitable medical grade material. Access disconnection, such as dislodgment of an arterial needle, a venous needle, or both, can be detected as previously discussed. Alternatively, the coupling device can be attached to the blood tubing set which is then attached to the dialysis machine in any suitable way.

In one embodiment, as the blood flows through the blood circuit during dialysis therapy, a controller and associated electronics generates a constant electric current or voltage, which is injected or passed into the flowing blood via electrical contacts. An electrode pair connected to the controller or other suitable electronic device can then be used to measure a voltage change across the fluid, impedance or other like electrical value to detect a change in impedance or the like across the vascular access region. In an embodiment, one electrode can be used to inject the electrical signal into the fluid circuit, while the other electrode of the pair can be used to sense a change in the electrical value and pass an electrical signal indicative of the same to the controller for processing and detection purposes. Upon dislodgment of at least one of the venous needle and arterial needle from the blood circuit or other suitable condition, an immediate and detectable increase in impedance or another related electrical property, can be measured as compared to the impedance or other suitable property measured under normal operating conditions.

It should be appreciated that the present disclosure can be modified in a variety of suitable ways depending on the medical therapy as applied. For example, the venous and arterial needles can be inserted into the vascular access of the patient at any suitable part of the patient's body, such as the upper arm, lower arm, upper thigh area or the like during dialysis therapy. As previously discussed, the present disclosure can be applied to a variety of different medical therapies including intravenous infusions, plasma exchanges, medication delivery, drug delivery, blood delivery and dialysis therapies, e.g., hemofiltration, hemodialysis, hemodiafiltration and continuous renal replacement.

Figure 2:
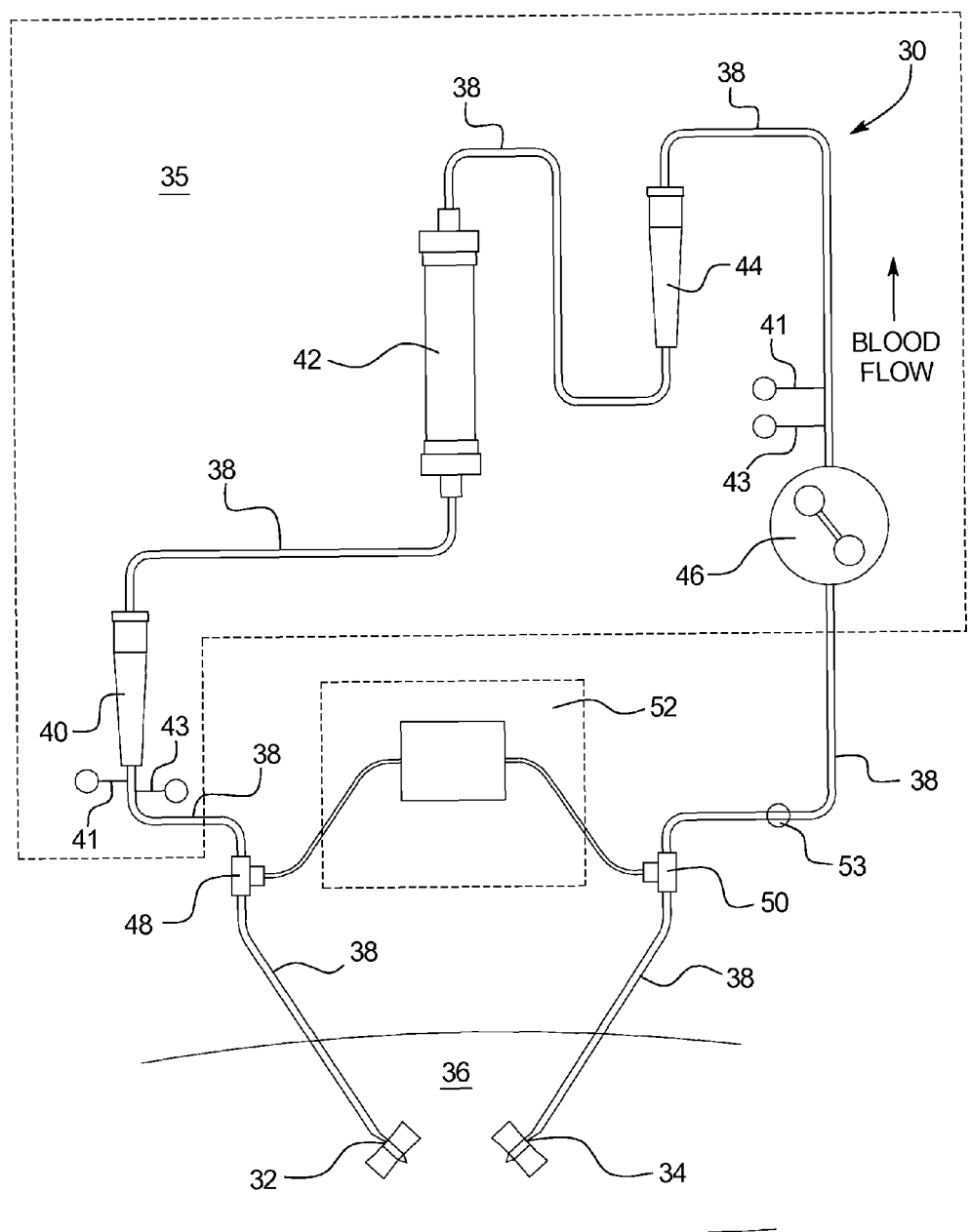
FIG. 2 is a detailed schematic view of connections in a hemodialysis machine.

As illustrated in FIG. 2, an embodiment of a system 30, such as a dialysis system, of the present disclosure is shown as applied during dialysis therapy. In this embodiment, system 30 includes a venous needle 32 and arterial needle 34 inserted within a patient access 36. The venous needle 32 and arterial needle 34 are connected to blood circuit 35 via venous line 26 and arterial line 28, respectively. Other tubes 38 connect various components of blood circuit 35 including, for example, a venous drip chamber 40, a dialyzer 42, an arterial drip chamber 44 and a blood pump 46. It should be appreciated that one or more of the components of the dialysis system can be provided within a dialysis machine coupled to the blood circuit.

As shown in FIG. 2, a first electrical contact coupling device 48 and a second electrical contact coupling device 50 are positioned in blood circuit 35 between venous needle 32 and arterial needle 34 and the tubes 38 connecting venous drip chamber 40, dialyzer 42, arterial drip chamber 44 and a blood pump 46. As used herein, the term "electrical contact coupling device," "coupling device" or other like term can mean any suitable device that can be used to connect an electrical contact to the fluid circuit. The electrical contact coupling device can be used to contact the electric connect to the fluid circuit allowing fluid contact and electrical connection with the fluid flowing through the fluid circuit as described below.

In addition to the electrical contacts, system 30 also includes temperature sensors 41 and pressure sensors 43. The temperature sensors are positioned in areas where the temperature is more likely to change as a result of operation of the system and affect the properties of the blood. These locations are adjacent the blood pump, where the frictional force of the pump may be transformed into heat, and near the outlet of the venous drip chamber 40. A higher temperature may affect a property of the blood directly, such as its impedance, and may also affect the properties of the tubing indirectly, for example, softening the tubing and making the tubing less resistant to the flow of blood. Other locations may be used. Pressure sensors are also placed in areas likely to be affected by operation of the hemodialysis system, such as adjacent the blood pump and also near the exit point of blood from the system as it is returned to the patient. If a venous access disconnect occurs, the blood pressure in this area is likely to show a sudden decrease.

In an embodiment, the electrical contact pair is connected to a controller 52 or other suitable electronic device. The controller can be used to inject an electric signal via the electrode pair and into the blood and/or other fluid as it flows through the blood circuit. This provides a conductor loop along which changes in electrical properties or values can be measured. Controller 52, which is coupled to the electrode pair, can also be used to measure this change. It should be appreciated that controller 52 can include a single electronic device or any suitable number of devices in electrical connection with the electrical contacts to input an electrical signal into the blood circuit to define a conductor loop, to measure a change in an electrical parameter or value associated with the conductor loop, or to perform any other suitable task, such as processing the detectable signal as discussed below.

The electrical signal is generated in one embodiment from a constant current that is supplied to the electrodes until dislodgment occurs. The voltage across the fluid (e.g., blood) circulating through the blood circuit can then be measured to detect a change in impedance due to changes in access conditions. However, it should be appreciated that any suitable electrical property and changes thereof can be monitored to detect needle drop-out or the like as previously discussed. As is well known, impedance is derived from the electrical resistance and capacitance of a circuit, since the square of the impedance equals the sum of the square of the resistance and the square of the capacitance. The impedance, resistance or capacitance may be used in the embodiments described herein.

As demonstrated below, the detection capabilities of the present disclosure are highly sensitive, specific and virtually immediate in response to access disconnection, such as needle dislodgment. Further, the electronic circuit of the present disclosure is relatively simple in design, in which only one electrode pair is necessary to conduct the disclosed direct measurement. This can reduce costs and effort as compared to known vascular access monitoring techniques that only employ non-invasive detection techniques, such as, capacitive couplers and induction coils.

Figure 3:
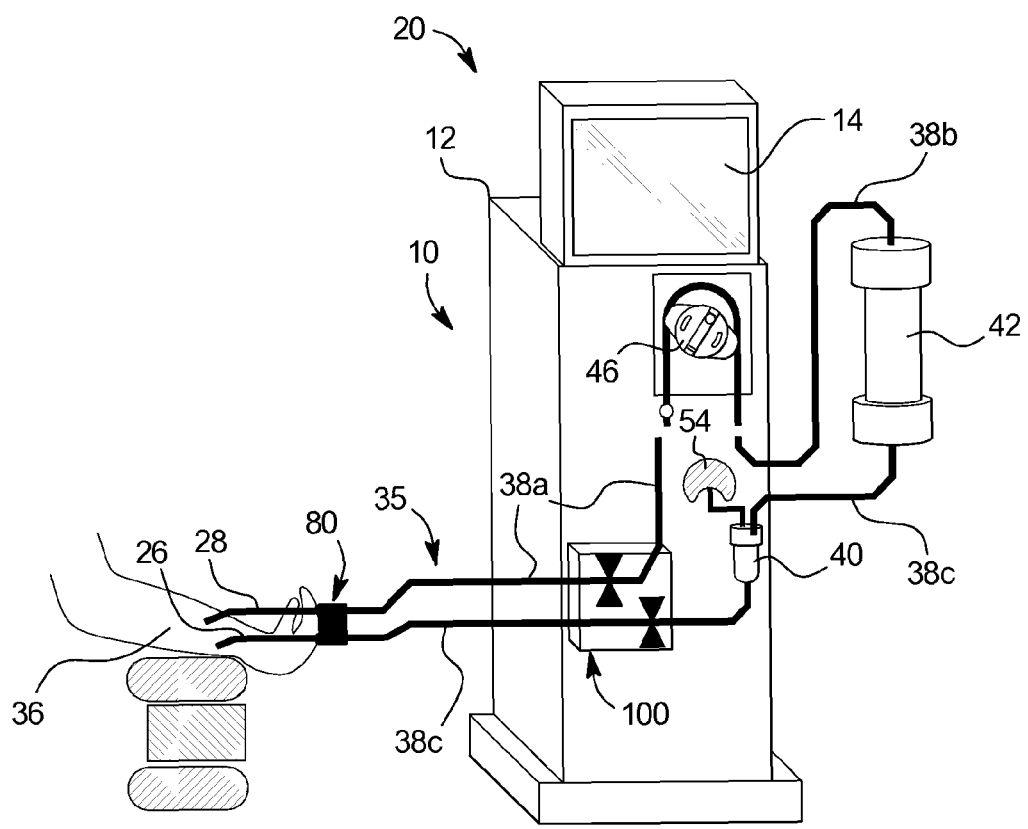
FIG. 3 is a perspective view of a hemodialysis machine showing alternate connections.

In another embodiment, the controller is divided into two portions, a portion near the patient, a detector module, and a portion that remains on or near the dialysis machine, as illustrated in FIG. 3. System 20 includes a dialysis machine 10, such as the one described above in connection with FIG. 1. For example, machine 10 includes a chassis or housing 12 and a touch screen 14. Machine 10 includes a blood circuit 35 having a venous line 26 and an arterial line 28 connecting to venous needle 32 and arterial needle 34, respectively, forming patient access 36. Arterial line 28 extends from patient access 36 to a detector module 80, which is shown in more detail below in connection with FIGS. 4-5. In general, detector module 80 includes electrodes that communicate electrically with contacts provided with venous and arterial lines 26 and 28, respectively, shown in FIG. 5. Alternatively, detector module 80 includes venous and arterial contact producing coupling devices 48 and 50, respectively, referenced above in connection with FIG. 1, which contact blood directly, obviating the need for contacts on the blood set. Detector module 80 also includes electronics capable of detecting an access disconnection and sending a remote or wireless signal to a protector module 100 described in more detail below in connection with FIG. 6.

A first tubing segment 38a of blood circuit 35 extends from detector module 80 to blood pump 46. A second tube segment 38b extends from segment 38a at blood pump 46 to dialyzer 42. A third tube segment 38c extends from dialyzer 42 to detector module 80. Venous line 26 extends from detector module 80 to patient access 36. As illustrated, detector module 80 is positioned to clamp one or more of tube segment 38a or 38c upon a sensing of a disconnection at patient access 36 by detector module 225. Venous drip chamber 40 is shown operating with tube segment 38c. Although not illustrated, an arterial drip chamber 44 can be placed additionally in tube segment 38a. Venous drip chamber 40 is shown operating with a pressure sensor 54.

It is expressly contemplated to provide system 20 including detector module 80 and protector module 100 as either an integrated part of machine 10, an option in ordering machine 10, or as a retrofit kit to an existing dialysis machine (or any other type of blood treatment or medical delivery machine described herein). Thus, in one embodiment, the electronics associated with detector module 80 and protector module 100 are independent from (except perhaps input power) the electronics of therapy machine 10.

Blood Variables and Properties

From a practical standpoint, there are a number of different process conditions that may influence a change in the baseline impedance over time. For example, a gradual drift or change in the baseline can occur due to a change in the characteristics, such as the hematocrit, plasma protein, blood or water conductivity or the like, of the blood or other suitable fluid during treatment. This can arise due to changes in the level of electrolytes or other components during dialysis therapy.

Figure 4:
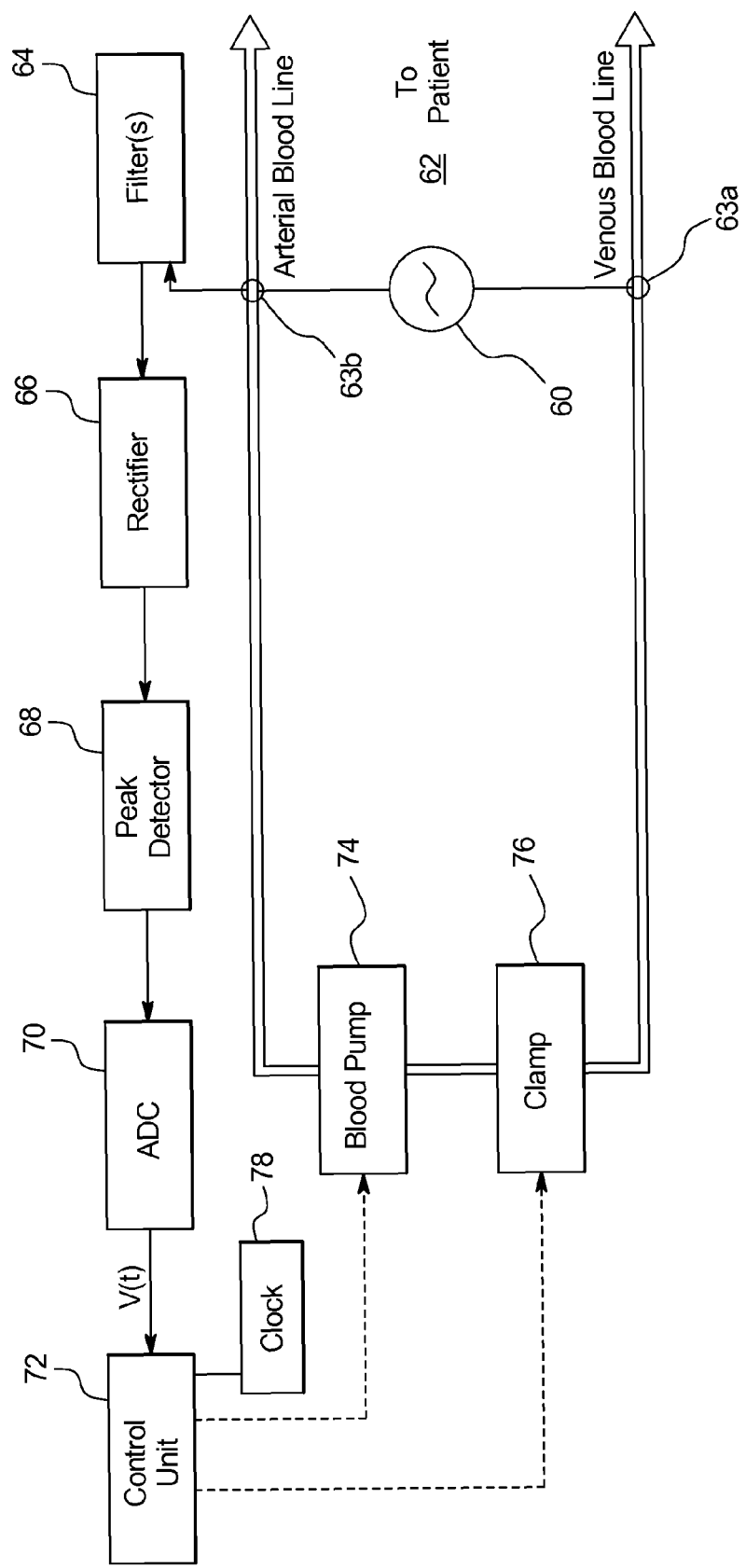
FIG. 4 is a schematic view of circuitry for use in embodiments of the present invention.

As illustrated in FIG. 4, the present disclosure can process a measurable voltage signal to correct for changes in baseline impedance over time. This can enhance the detection capabilities of the present disclosure as previously discussed. In an embodiment, a current source 60 or the like generates an electric current to pass through the blood as it circulates into, through and out of the patient along the extracorporeal blood circuit 62, which connects the patient via venous and arterial needles to the dialysis system including a variety of process components. The electric current is injected into the blood circuit via a first electrical contact 63a to define a conductor loop or pathway along the blood circuits. The current is maintained at a constant level until dislodgment occurs in one embodiment.

A second electrode 63b is used to sense voltage or the like along the conductor loop and then pass a signal indicative of the voltage or changes in the voltage thereof to an electronic device for detection and processing as previously discussed. The voltage signal can be measured and processed in any suitable manner.

In an embodiment, the signal is passed through a series of components including a filter or filters 64 which can act to filter noise from the signal, particularly noise derived from the rotation from the pump in order to minimize a false negative positive detection of needle dislodgment (or both), a rectifier 66, a peak detector 68 and an analog to digital converter ("ADC") 70 to digitize the signal. The digital signal can then be stored in a computer device for further processing. The voltage signal is continually measured and processed over time. With each measurement, the digitized signals are compared to evaluate changes due to baseline changes associated with variations in process conditions over time, such as a change in the characteristics of blood as previously discussed. If a baseline change is determined, the digitized signal can be further processed to correct for the change in baseline.

The voltage data is continually sent to a control unit 72 coupled to the ADC. The control unit continually performs a calculation to determine whether a change in impedance or the like in response to needle dislodgment has occurred. In one embodiment, dislodgment of an access device is detected when $[V(t)-V(t-T)]>C$, where t is elapsed time, T is the period of blood pump revolution, C is a constant and $V(t)=I_o*Z$, in which $I_o$ is current and Z is the impedance of the bloodline.

The impedance of the bloodline is a function of the impedance associated with patient's vascular access and the impedance associated with various components of the dialysis system, such as the dialyzer, as previously discussed. The controller or control unit 72 thus also can track the time period for each revolution of the pump and the frequency of the revolutions of the pump, that is, the pump speed. Given these data, the control unit also can track the volume of blood being pumped.

As will be obvious to those having skill in art, the pump revolutions or speed may be counted by an encoder on a shaft or actuator of the pump. Alternatively, pump roller position can be tracked by electrically by the pump controller, which can also track the position of the armature or rotor of the blood pump, such as by commutation pulse detection, and thus the roller position or position of other actuation portion of the pump. This same capability allows the controller to also keep track of the position of the pump rollers, piston, diaphragm, or other motive force used in the dialysate or ultrafiltrate pump.

If disconnection of the patient from the blood circuit is detected, the microcontroller or control unit 72 can be utilized to minimize blood loss from the patient. In an embodiment, the controller is in communication with a dialysis system as applied to administer dialysis therapy including, for example, hemodialysis, hemofiltration, hemodiafiltration and continuous renal replacement therapy. This communication can be either hard-wired (i.e., electrical communication cable), a wireless communication (i.e., wireless RF interface), a pneumatic interface or the like. The microcontroller communicates with the dialysis system or device to shut off or stop the blood pump 74 associated with the hemodialysis machine and thus effectively minimize the amount of blood loss from the patient due to needle dislodgment during hemodialysis.

The controller can communicate with the dialysis system in a variety of other ways. For example, the controller and hemodialysis machine can communicate to activate a venous line clamp 76 for preventing further blood flow via the venous needle thus minimizing blood loss to the patient. In an embodiment, the venous line clamp is activated by the controller and attached to or positioned relative to the venous needle such that it can clamp off the venous line in close proximity to the needle. The dialysis system can also be programmed to shut off the blood pump at the same time.

In an embodiment, an alarm can be activated upon detection of blood loss due to, for example, needle dislodgment during dialysis therapy. Once activated, the alarm (i.e., audio, visual or the like) is capable of alerting the patient, a medical care provider (i.e., doctor, registered nurse or the like), or a non-medical care provider (i.e., family member, friend, or the like) of the blood loss due to, for example, needle dislodgment. The alarm function is particularly desirable during dialysis therapy in a non-medical facility, such as in a home setting or self-care setting where dialysis therapy is typically administered by the patient and/or a non-medical care provider in a non-medical setting or environment.

The alarm activation, for example, prompts the patient to check that the blood pump has been automatically shut off, so that blood is minimized. Thus, the patient has the ability to act without the assistance of a third party (i.e., to act on his or her own) to ensure that responsive measures are taken to minimize blood loss. The alarm can thus function to ensure the patient's safety during the administration of dialysis therapy, particularly as applied to home hemodialysis treatments in which at least a portion of the dialysis therapy can be administered while the patient is sleeping.

Figure 5:
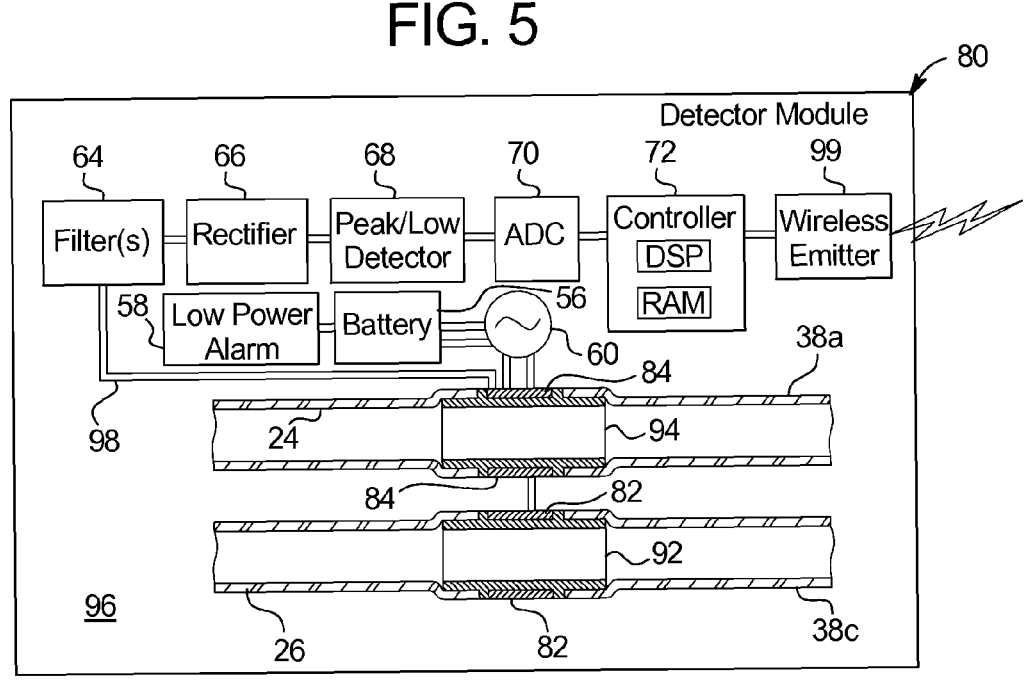
FIG. 5 is a schematic view of detecting circuitry for use in embodiments of the present invention.

Referring additionally to FIG. 5, detector module 80 in one embodiment monitors the electrical impedance of blood in the extracorporeal circuit, as described herein, and generates an alarm causing protector module 100 to clamp at least one of arterial tube segment 38a and venous tube segment 38c of blood circuit 35 should a venous or arterial dislodgement at patient access 36 occur.

Besides detector module 80 and protector module 100, system 20 also includes a disposable portion in one embodiment as shown in FIG. 5. The disposable portion operates with detector module 80 and includes two contacts 92 and 94, which make electrical contact with flowing blood, or clamp over the blood-set tubing. In a retrofit embodiment, prior to treatment, disposable electrodes 82 and 84 are inserted into blood circuit 35. As shown, arterial tube 24 and tubing 38a are fitted sealingly over contact 94, while venous tube 26 and tubing 38c are fit sealingly over contact 92. Or, blood circuit 35 can be provided with contacts 92 and 94 preinstalled. In any case, contacts 92 and 94 can be metallic components or be made of a conductive polymer. When contacts 92 and 94 are provided with blood circuit 35, detector module 80 is provided with two electrodes 82 and 84, which make electrical contact with contacts 92 and 94 of blood circuit 35, respectively. Electrodes 82 and 84 in the illustrated embodiment are provided as spring clips that hold contacts 92 and 94 and associated tubing 24, 26, 38a and 38b of blood circuit 35 in place physically.

Detector module 80 senses a needle dislodgement by measuring the impedance between the electrodes as is described herein. To do so, detector module 80 injects an electrical current into the flowing blood. Current injection is performed either invasively (direct blood contact, e.g., from source 60, through electrode 82 or 84 to contacts 92 and 94) or non-invasively (with no contact as discussed below). In one embodiment, detector module 80 induces and measures impedance directly and invasively. Invasive measurement requires that disposable contacts 92 and 94 be placed in physical contact with the flowing blood in blood circuit 35.

Alternative to invasive measurement, detector module 80 can be configured to measure impedance non-invasively, for example by capacitive coupling, or via magnetic induction of current. To achieve capacitive current coupling, detector module 80 places capacitive electrodes (not illustrated) over blood circuit 35. Detector module 80 then applies an alternating voltage to the outer electrodes to induce an ionic current that travels from one electrode to the other. In an inductive embodiment, detector module 80 includes a magnetic coil (not illustrated), which is wrapped around the blood tubing. Detector module 80 induces an electrical current using the magnetic coil. The alternating current applied to the coil changes the magnetic flux in the coil and induces an ionic current in the blood.

Whether the current is introduced to the blood directly, capacitively, or inductively, detector module 80 includes electronics configured to measure a change in electrical impedance. Detector module 80 in an embodiment is a small, lightweight, battery-operated device that connects to disposable access disconnect system electrodes 92, 94. Detector module 80 includes an excitation voltage source 60, which is converted to an electrical current that is induced into the blood. The returning current (which is indicative of an impedance of blood circuit 35) through one of the contacts 92, 94 is converted to a voltage, measured and processed. Alternatively, detector module 80 measures a voltage across contacts 92, 94, which is also indicative of an impedance of blood circuit 35. In one embodiment, the effects of changes of any of the blood variables and properties are stored in a look-up table accessible to the controller or to its memory. These values may be used for calculating first and subsequent values for a minimum or maximum value for an access disconnect Therapy Variables and Properties As illustrated, detector module 80 includes any one or more of voltage source 60 (connected electrically to contacts 92, 94 through electrodes 82, 84 of module 25), filter(s) 64, rectifier 66, peak detector 68, analog to digital converter ("ADC") 70, microcontroller control unit 72 (FIGS. 4-5), clock 78 and a wireless emitter 99, which is set to communicate with protector module 100. The electronics of detector module 80 in one embodiment are provided on a printed circuit board ("PCB") 96 and connected electrically to each other via traces 98. The microcontroller can also store inputs from an operator, such as when therapy has begun, when a drug or medicine was infused into the patient, and when a bolus of saline or heparin was administered. The clock may be used to time intervals during the blood treatment, such as the time elapsed since therapy was begun, or the time interval since a drug or a bolus was administered. All or any of these inputs may have an effect on a property of the blood, such as its impedance or capacitance. The look-up table stored in the memory of the therapy controller, or accessible to the controller, includes an estimate of the effect any or all of these therapy values.

Controller 72 can include a memory, such as a random access memory ("RAM"), and a processor, such as a digital signal processor ("DSP"). RAM stores software and buffers the digital signals from ADC 70, while the DSP processes the buffered signals using the stored software. Upon an access disconnection, the impedance of blood circuit 35 changes dramatically, as do the resistance and the capacitance. The microcontroller senses this change and sends a signal though wireless emitter 99 to receiver 101 of protector module 100. Emitter 99 and receiver 101 in one embodiment operate via radio frequency ("RF"), but alternatively operate via microwave or other suitable frequency, or may be hard wired together.

Figure 6:
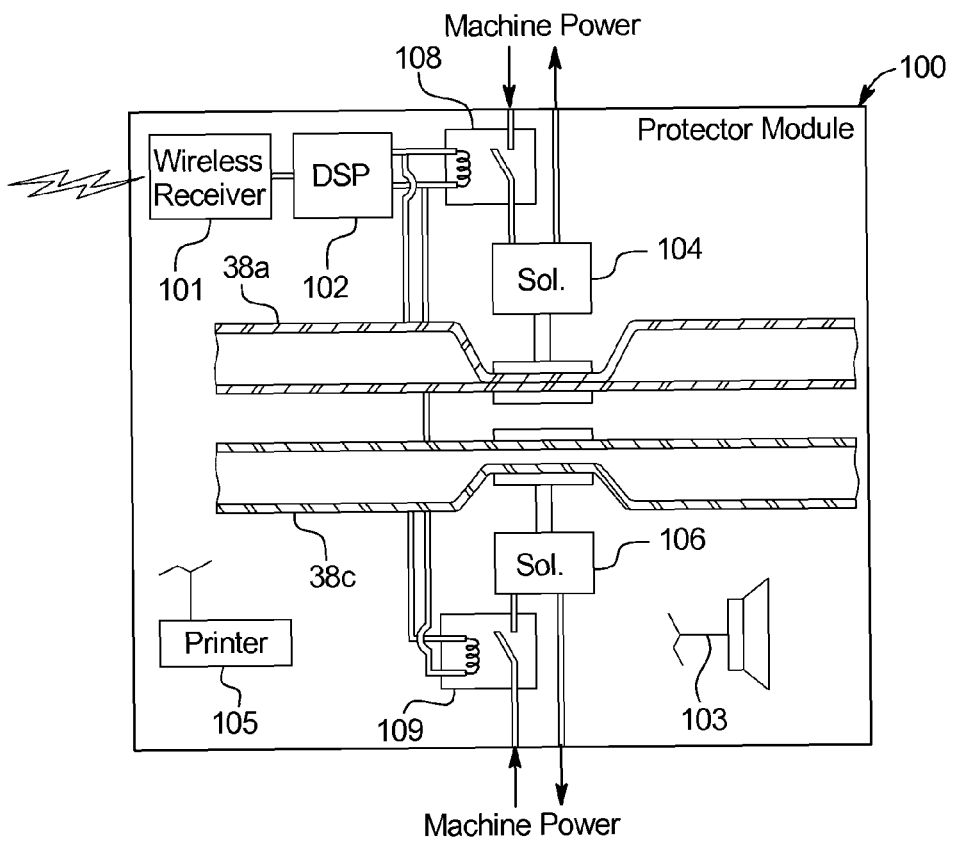
FIG. 6 is a schematic view of controlling circuitry for use in embodiments of the present invention.

Protector module 100 is shown in more detail in FIG. 6. Protector module 100 includes wireless receiver 101, which is set to look only for the particular transmission from its corresponding emitter 99 and detector module 80. In this manner, multiple machines 10 employing system 20 can be set side-by-side. In an embodiment, the signal received by receiver 101 is digitized or is otherwise conditioned by receiver 101 to be in a form suitable for a processor 102, such as a digital signal processor ("DSP") to accept. In an embodiment processor 102 is set to look for a signal from receiver 101 upon which processor 102 causes clamps or occluders to close one or both of arterial tubing 38a and venous tubing 38c fully or partially as described in more detail below. Clamps or occluders in one embodiment are solenoid valves 104, 106 powered from machine 10. Processor 102 operates solid state switches 108, 109 which close when directed to allow operating power to reach the solenoids. Other techniques or components may be used.

Upon receiving an access disconnection signal, protector module 100 is configured to clamp at least venous tubing 38c and in one embodiment both venous tubing 38c and arterial tubing 38a. Clamping both venous tubing 38c and arterial tubing 38a, however, could cause a pressure spike to occur more quickly in venous tubing 38c, which in turn is sensed more quickly by pressure transducer 54 coupled to venous drip chamber 40. A pressure spike sensed by pressure transducer 54 causes circuitry, e.g., within machine 10, to shut down blood pump 46, in one embodiment, before the pressure can increase enough to damage venous tubing 38c. This circuitry can already be present within machine 10, so that it would not have to be added to system 20. Alternatively, protector module 100 can include the necessary circuitry.

In an alternative embodiment, if pressure transducer or sensor 54 is not provided or if the transducer is simply for reading out pressure rather than for control, both venous tubing 38c and arterial tubing 38a bloodlines are occluded. Arterial bloodline 38a is occluded completely to prevent any further blood from being lost (other than what is already in the extracorporeal circuit). Venous bloodline 38c is occluded partially to slow down loss of blood already in the extracorporeal circuit, while preventing damage to bloodline 38c due to an excess pressure. Protector module 100 may also include a speaker 103 to warn the patient or the caregiver than an access disconnect has occurred or that the value of the criterion is approaching a limit or has exceeded a limit. Alternatively the module may include a printer 105 to print a warning or an alert to the patient or the caregiver.

Detector module 80 and protector module 100 are relatively simple, inexpensive devices. It is contemplated to mount protector module 100 to the front 13 of machine 10, however, protector module 100 can be mounted alternatively to any part of machine 10 to which venous tubing 38c and arterial tubing 38a can reach and still reach patient access 36. Protector module 100 in one embodiment is powered from machine 10. Detector module 80 can be battery powered. To that end, battery 56 of detector module 90 in one embodiment is rechargeable and protector module 100 in one embodiment includes an electrical socket to receive a power recharging connector of detector module 80 for recharging the battery 56 of and storing detector module 80 between uses.

Detector module 80 in one embodiment includes a low power alarm 58, which alerts a patient or caregiver when detector module 80 needs to have its battery 56 recharged or replaced. Battery 56 powers voltage source 60 and any one or more of the components needing power, including filter(s) 64, rectifier 66, peak detector 68, ADC 70, controller 72, alarm 58 and wireless emitter 99. Although not illustrated, alarm 58 can interface though emitter 99 to cause protector module 100 to clamp the blood lines 38a and 38c and potentially stop blood pump 46 until battery 56 of detector module 80 is recharged. To that end, detector module 80 is configured to accept AC power (not illustrated) in one embodiment, so that therapy can be resumed without having to recharge or replace a battery immediately.

Either one of detector module 80 and protector module 100 can include a small monitor and/or data port (not illustrated) to download stored information in real time or later for diagnostic purposes. In one embodiment such apparatus is provided on detector module 80, so that retrieved data does not have to be sent to protector module 100. Alternatively, e.g., for power or space reasons, monitor and/or data port are provided with protector module 100. In such case, necessary software and processing capability are added to protector module 100.

The data retrieved can include any one of peak impedance (e.g., low blood flowrate), low impedance (e.g., high blood flowrate), average impedance (e.g., average blood flowrate), frequency of impedance spikes, etc. For example, it is contemplated that the blood pump's cyclical occlusion of blood circuit 35 will create impedance spikes having a signature frequency. If the frequency changes it could be a sign of blood pump wear or improper functioning or signal that the patient is causing impedance spikes, e.g., by kinking a line. This data retrieval and analysis can be performed by any of the systems described herein.

Figure 7:
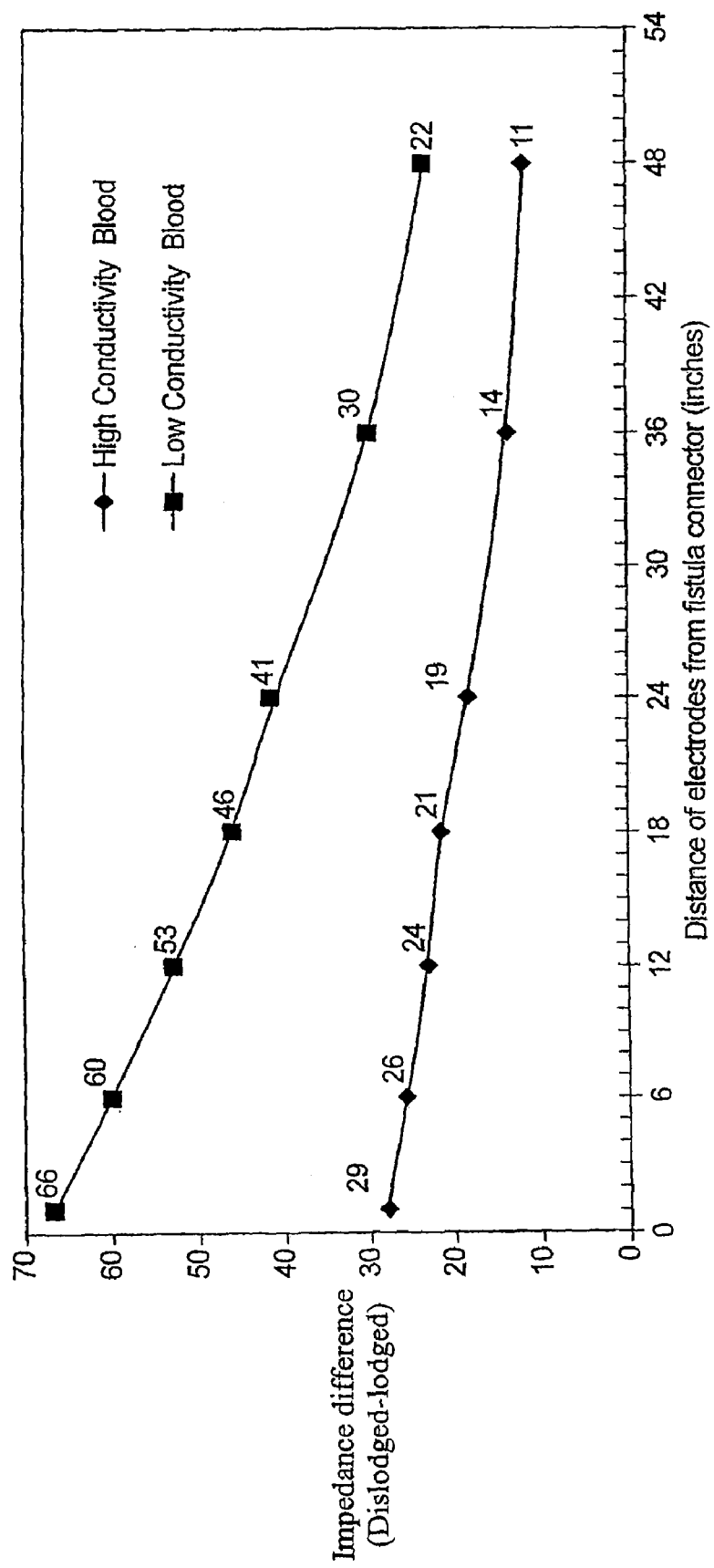
FIG. 7 is a graphical depiction of the differences in impedance with differing bloods and different distances between electrical contacts.

Data in FIG. 7 show the difference in impedance for two patients with blood of differing conductivity. The ordinate is the distance of the electrodes from the fistula connector (at the access site), while the abscissa is the increase in impedance value from a properly placed access needle to one that has become dislodged. The upper curve, for a patient having blood with low conductivity, has a higher slope, which indicates greater dependence of the impedance value on the electrode distance. The lower curve, with a patient having blood with higher conductivity, shows less dependence (a lower slope) on electrode distance. Overall, these data suggest that there is a great variability in the selected criterion, impedance of the circuit, between patients and, for a particular patient, a three-fold variability in the absolute value of the change to be expected in a disconnect—66 vs. 22 for one patient, 29 vs. 11 for the other.

An Adaptive Algorithm

Embodiments use an adaptive algorithm that includes consideration of first values of a number of the properties discussed above and used as parameters in the algorithm or program. For convenience sake, the physical properties, such as temperature, pressure, pH and the like, may be considered as blood variables or properties. Other considerations, such as elapsed time of the therapy, administration of a drug or other solution to the patient's bloodstream, and so forth, may be termed as therapy values, and may also be used as parameters in the algorithm.

In one embodiment, the adaptive algorithm begins with already-entered values for these parameters and properties, and using these values, estimates a first set of criteria for operating limits for the hemodialysis machine. The limits may be high and low limits for impedance or high and low limits for capacitance or resistance. In another embodiment, each therapy session begins with fresh values, possibly with some values retained as default values, such as perhaps, an inlet blood temperature. Once therapy has begun, the therapy is monitored for at least a plurality of these properties, and when one or more of the properties changes, the adaptive algorithm re-calculates new limits for the high and low values. Thus, by keeping track of two or more variables, as discussed above, the algorithm is able to adjust itself to changing circumstances for both the patient's blood, the therapy, and the therapy machine.

Figure 8:
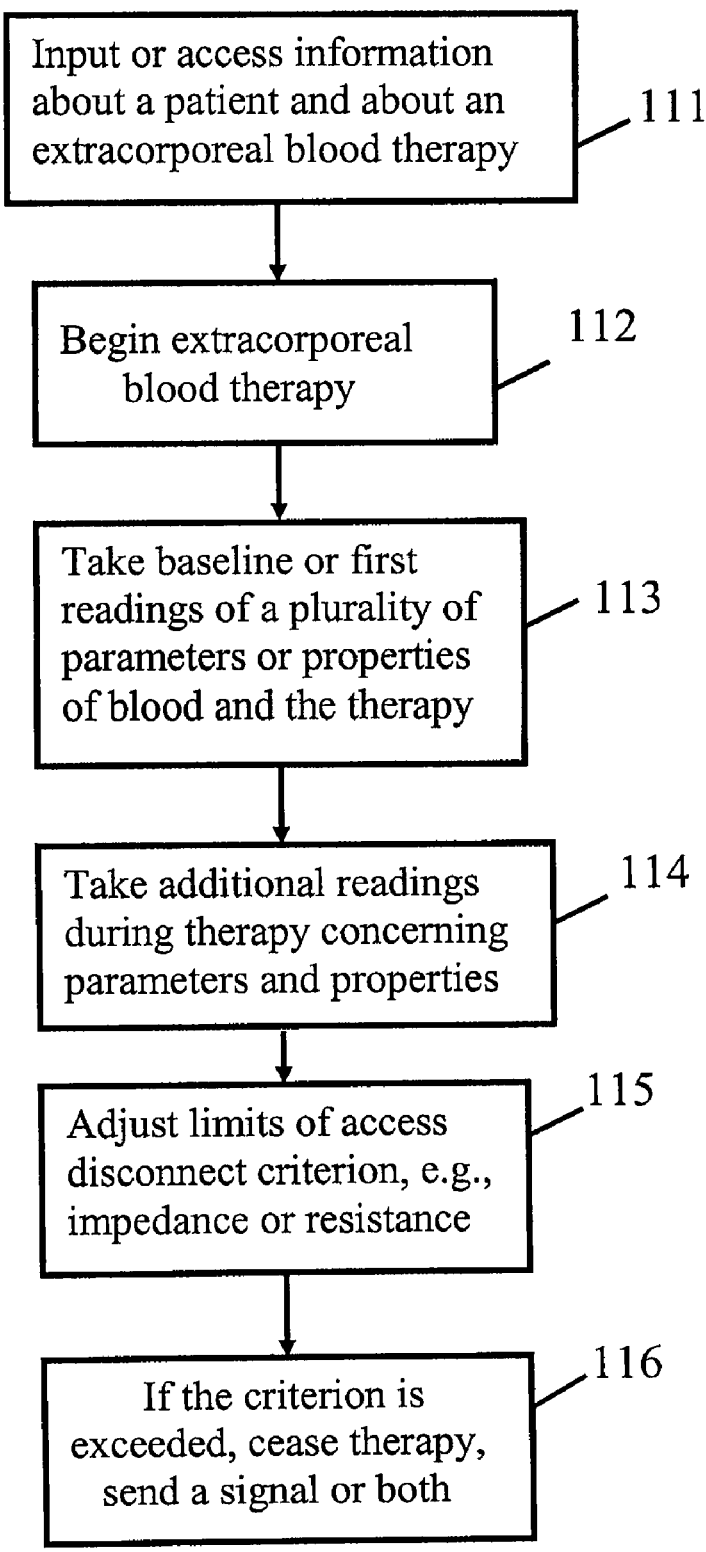
FIG. 8 is a flowchart for a method of operating an extracorporeal blood circuit using an adaptive algorithm.

A simplified example of the algorithm is depicted in the flowchart of FIG. 8. As noted, a first step 111 is to input or access information about the patient and the extracorporeal blood therapy that is to be administered to the patient. The blood therapy is begun 112. Baseline or first readings of a plurality of parameters or properties of the blood or the therapy machine are taken 113, processed, and input to the computer program constituting the adaptive algorithm. This step may take place before or after therapy has begun. Since the computer program will run quickly, it may be more useful to update the program with these first or baseline readings immediately after therapy has begun.

Once the first values have been taken and therapy begins or continues, a number of additional readings may be taken 114 as often as desired to insure that access disconnection does not occur. For example, readings may be taken once per second. For this application, access disconnect, readings should probably be taken from about 10 times per second to about once every two seconds, i.e., 0.5 Hz to about 10 Hz. In other embodiments, readings may be taken at least twice per second, i.e. 2 Hz. For temperature, time, position, impedance, resistance, capacitance, pressure, or other similar, on-line instantaneous measurements, such readings are readily accomplished. For other properties, such as a hematocrit value, or consideration as to whether a drug has been administered, the changes occur infrequently. Users will make an entry into the computer, informing the controller as to the new value of the variable, when a substance has been administered, and similar changes. The algorithm accepts the new information and re-calculates 115 the alert criterion or criteria for the therapy. Therapy continues, and if the criterion value, such as a minimum or maximum impedance, is exceeded, the microcontroller sends a signal 116 to cease therapy, alert a caregiver, sound an alarm, or take other action.

The above description has included a discussion of a number of properties of blood, and a number of operating parameters of an extracorporeal blood therapy, of which hemodialysis is one. Blood properties include the temperature of the blood as measured by the temperature sensors on the therapy machine or on the patient, and the pressure of the blood, as measured by pressure sensors on the therapy machine or on the patient. Other blood properties include a hematocrit value, or any value of a important blood chemistry element, such as one of the "basic 20," especially one that will be affected by the progress of the hemodialysis procedure, such as uric acid content or carbon dioxide. pH of the blood is an important property. Note that it is not necessary that a property of the blood be measured on-line. Periodic tests taken by the patient or a caregiver during the progress of the therapy are also representative of properties of the blood. Of course, these properties include properties that are measured on-line, such as the impedance, capacitance, and resistance discussed above.

Besides blood properties, parameters of the therapy change while the therapy progresses. The most basic parameter may be the length of time that the therapy has continued, or the elapsed time. Other parameters that may be of interest include the dialysis fluid temperature, the pump speed, the pump temperature, whether and when the patient has been administered a medicine, such as a drug, whether the patient has been administered a bolus of saline or heparin, and so forth. A look-up table stored in the memory of the therapy controller, or accessible to the controller, includes an estimate of the effect any or all of these therapy values.

Description of the Algorithm

Figure 9A:
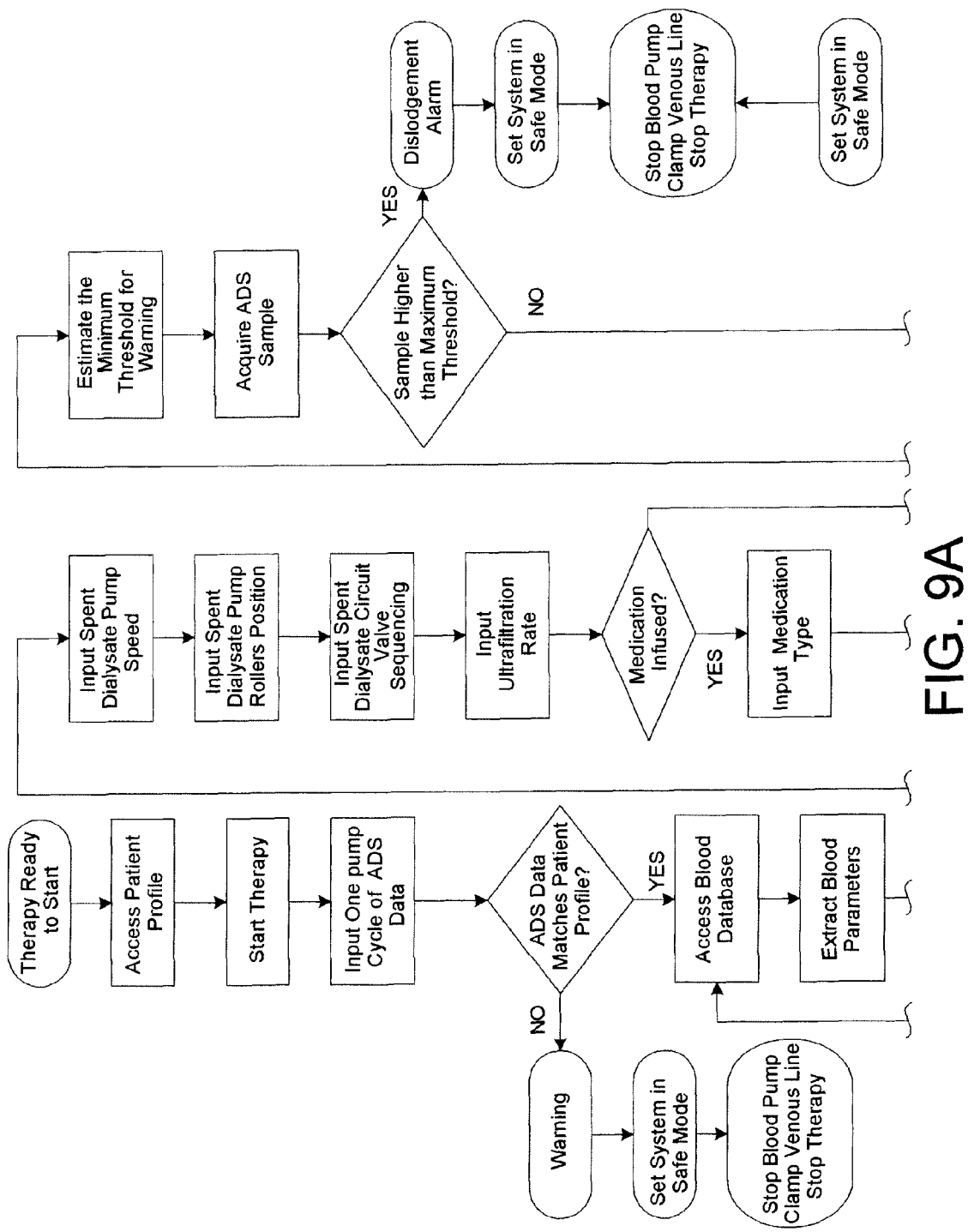
FIGS. 9A to 9C illustrate a more detailed flowchart for a method of using an adaptive algorithm to protect a patient from access disconnect.
Figure 9B:
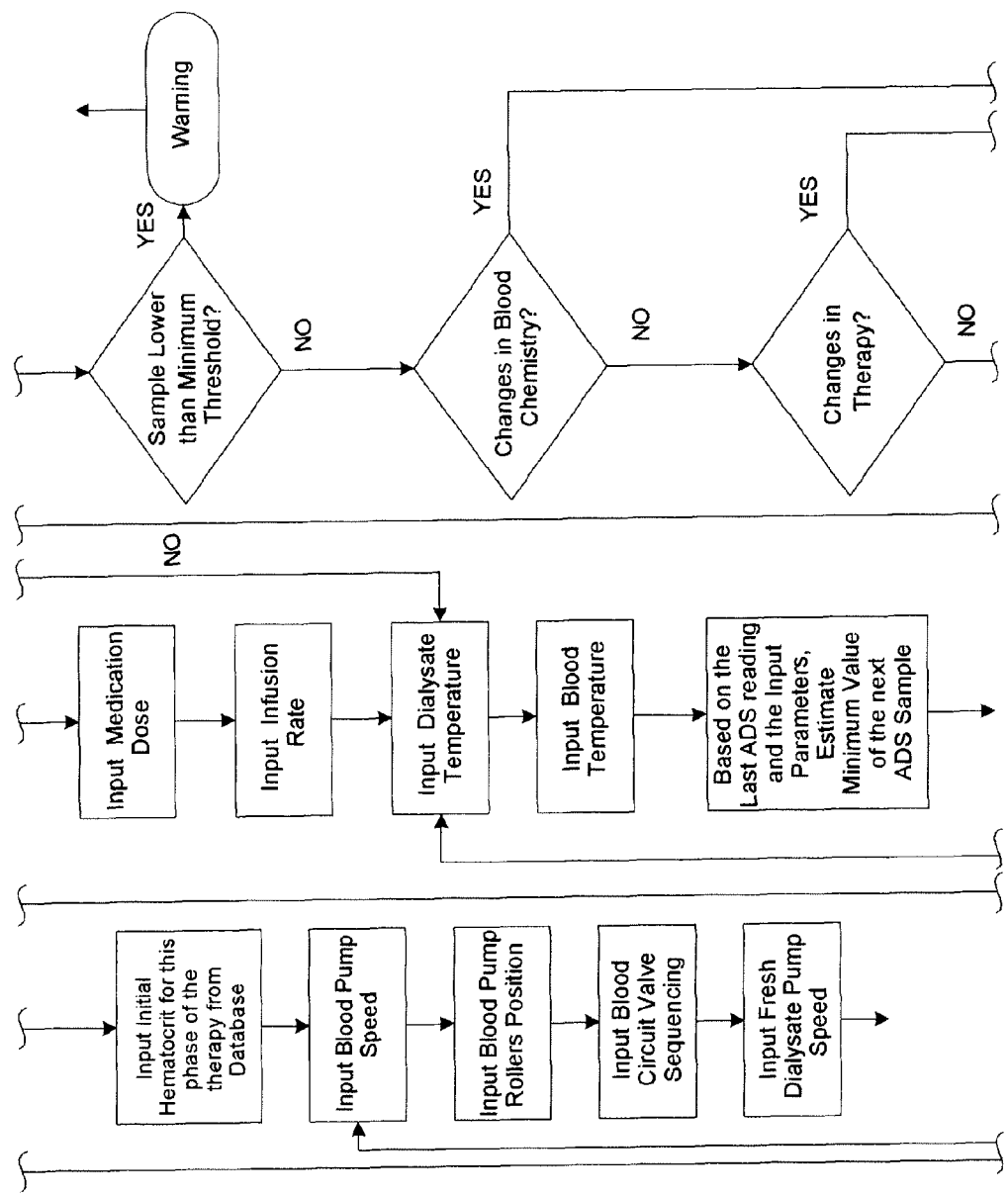
Figure 9C:
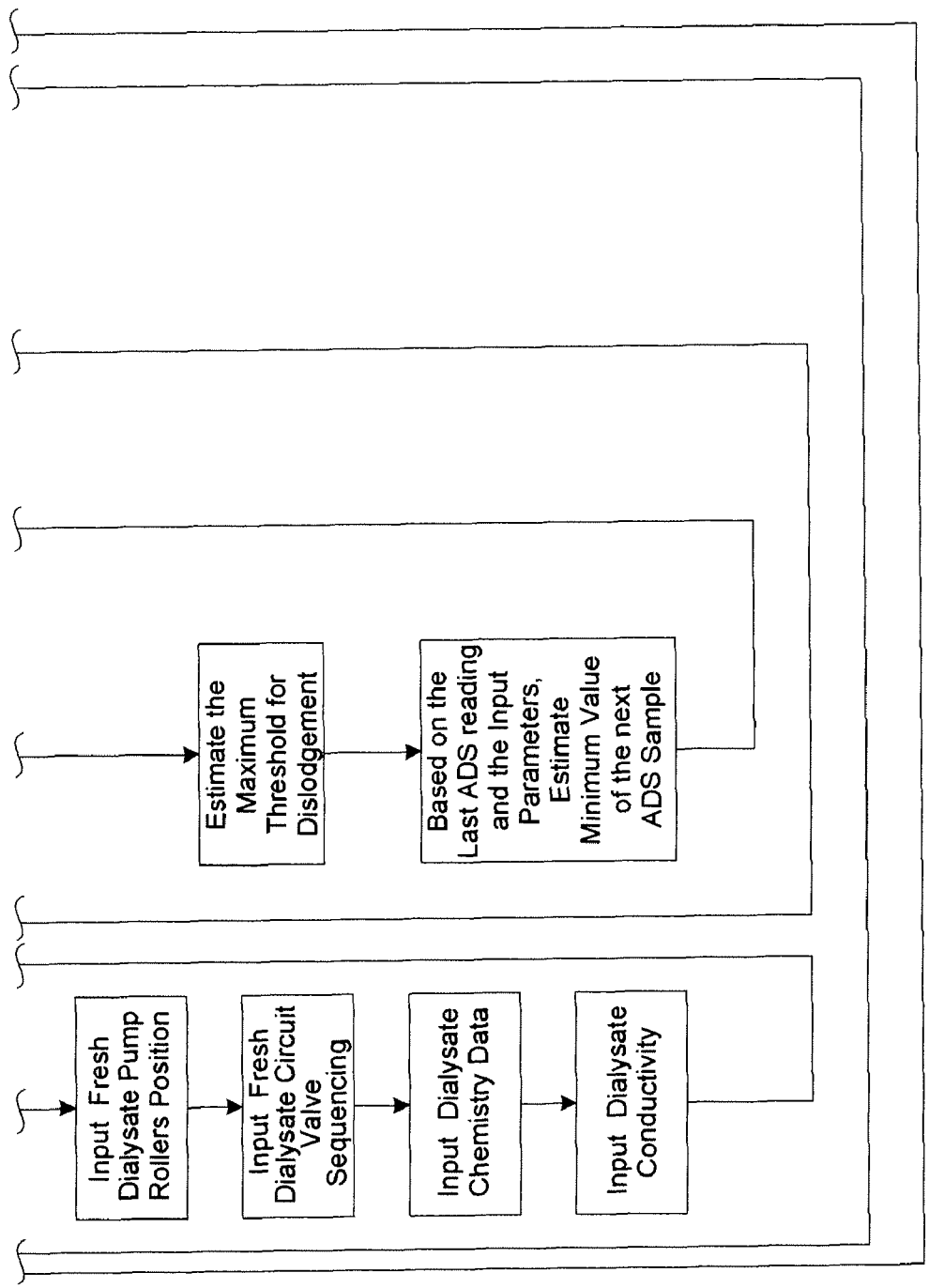

The algorithm has several embodiments. Not all of the numerous features or steps shown in FIGS. 9A to 9C need be present in every embodiment. The algorithm is most conveniently used in the form of a computer program, which may be stored in a memory of the computer or in another device, such as an EEPROM, for operable connection to the computer. The computer program begins, and initially accesses data for the patient for whom therapy is contemplated. The data includes patient identification data, as well as data concerning previous readings on properties of the patient's blood, such as prior electrical properties, blood chemistry properties, and the like. If this is the first therapy for the patient, or previous data is unavailable, then initial readings may be taken, or data may be input or accessed Numerous input data include, for example, a hematocrit value and other properties of the patient's blood. Variables or "properties" from the therapy machine are also input, including for example: the therapy start time; the blood pump speed; the blood pump rollers position; the position of the input blood valves and the desired valve sequencing; the fresh and spent dialysate pump speeds; the fresh and spent dialysate pump rollers position; the dialysate chemistry data and electrical properties, such as impedance and conductivity; the position of the spent dialysate valves and the desired valve sequencing; and the desired ultrafiltration rate.

The program also takes account of variables that may affect this particular therapy, such as medication received by the patient, especially medication administered just before or during the therapy, since this medication may affect the patient and the criterion or criteria selected for monitoring the access connection. Thus, the program accepts or queries the user or the caregiver for information on the medication type, the quantity or dose, and the infusion rate. This information includes, for example, a bolus or saline or a dose of heparin that is administered during the therapy. It is also useful to input the temperatures of the patient's blood and the dialysate, since both of these may affect the electrical properties of the patient's blood. Other properties may also be used, such as the input and output pressures of the patient's blood at the hemodialysis or other therapy machine.

Based on these properties, the algorithm calculates at least a minimum or a maximum value for the access disconnect criterion, such as minimum and maximum values for impedance or minimum and maximum values for conductivity. When subsequent readings are taken for one or more of these properties, the values for the criteria are re-calculated and the new values are used to determine when an access disconnect has occurred. The program can also determine when other types of new data have been input, for example, new information of blood chemistry properties, medicine administered, changes to the therapy, and so forth. The program also keeps track of the length of time therapy has continued, since the conductivity and impedance of blood is expected to change dramatically as dialysis proceeds. When the particular criterion has been exceeded, an alarm is sounded or an alert is sent to the patient or caregiver. Other steps may also be taken, such as to place the therapy system in a safe mode, to stop the blood pump, to clamp the venous line and to stop the therapy.

The algorithm disclosed herein receives input from the patient profile, blood chemistry database, therapy parameters and the last acquired impedance sample to estimate what the maximum and minimum acceptable levels for the next impedance value will be, thus creating an envelope within which no alarm will occur. Therapy is begun and additional readings or samples are taken. If the next sample falls outside the maximum or minimum the algorithm causes the instrument to stop the therapy and default to a safe state where the blood pump stops, the venous line lamp closes and a warning, an alert, or an alarm is issued. The dynamic nature of the algorithm allows setting margins for monitoring the access connection based on the patient therapy characteristics and chemistry evolution through the treatment, instead of using fixed statistical data. It allows narrowing of the margins for alarms and increasing the safety of the therapy.

It should be understood that various changes and modifications to the presently preferred embodiments described herein will be apparent to those skilled in the art. Such changes and modifications can be made without departing from the spirit and scope of the present subject matter and without diminishing its intended advantages. For instance, the steps of the method claims below need not be performed strictly in their order of appearance in the claims. It is therefore intended that such changes and modifications be covered by the appended claims.

What is claimed is:

1. A method for detecting an access disconnection, the method comprising:
   inputting or accessing information about a patient for an extracorporeal blood therapy;
   inputting or accessing at least one value for an alert criterion for an access disconnection;
   beginning the extracorporeal blood therapy;
   reading a first of a plurality of properties concerning the therapy and blood of the patient, the plurality of properties selected from the group consisting of a distance between access needles for the extracorporeal therapy, a temperature of a portion of an extracorporeal blood therapy machine, a speed of a pump of the extracorporeal blood therapy machine, an administration of a bolus to the extracorporeal blood circuit, and a dialysate temperature;
   proceeding with the extracorporeal blood therapy;
   reading a second of the plurality of properties concerning the therapy and the blood of the patient;
   calculating a change in the at least one value for the alert criterion based on the reading of the second of the plurality of properties; and
   adjusting the at least one value for an alert for the access disconnect criterion.

2. The method of claim 1, wherein the plurality of properties is further selected from the group consisting of: an electrical property of the blood of the patient; and a value of a blood chemistry component of the patient.

3. The method of claim 1, further comprising taking a reading of the property corresponding to the access disconnect criterion and sending a signal if the reading exceeds the value of the access disconnect criterion after the step of adjusting.

4. The method of claim 1, wherein the extracorporeal blood therapy comprises hemodialysis.

5. A method for detecting an access disconnection, the method comprising:
   inputting or accessing information about a patient for an extracorporeal blood therapy;
   selecting or accessing at least one electrical property value of an electrical circuit selected from the group consisting of the patient and an extracorporeal blood therapy machine as an alert criterion for an access disconnection;
   beginning the extracorporeal blood therapy;
   reading a first of a plurality of properties concerning the therapy and blood of the patient, the plurality of properties selected from the group consisting of a distance between access needles for the extracorporeal blood therapy, an elapsed time of the therapy, a temperature of at least a portion of the extracorporeal blood therapy machine, a speed of a pump of the extracorporeal blood therapy machine, administration of a bolus to the extracorporeal blood circuit; and a dialysate temperature;
   proceeding with the extracorporeal blood therapy;
   reading a second of the plurality of properties concerning the therapy and the blood of the patient;
   calculating a change in the electrical property value of the alert criterion based on at least one change in the plurality of properties; and
   adjusting the alert criterion value.

6. The method of claim 5, wherein the plurality of properties are further selected from the group consisting of a value of a blood chemistry component of the blood of the patient.

7. The method of claim 5, further comprising sending an alert or sounding an alarm if the second reading of the electrical property value exceeds the alert criterion value after the step of adjusting.

8. The method of claim 5, further comprising applying a voltage or a current to the electrical circuit in order to take the first and second readings.

9. An access disconnect detection system, comprising:
   arterial and venous contacts configured for use with an extracorporeal blood therapy machine for administering a therapy;
   an electrical circuit connected to the contacts, the electrical circuit configured for sensing at least one electrical property sensed by the contacts;
   at least one sensor configured for sensing a plurality of properties concerning the patient or a component of the extracorporeal blood therapy machine, the plurality of properties selected from the group consisting of a pressure, a speed, an infusion rate, a presence or absence of a bolus, a presence or absence of a medication, a duration of time, and a temperature;
   a computer having a memory, the computer configured for receiving and storing values for the plurality of the properties concerning the patient and the extracorporeal blood therapy machine; and
   a computer program on a computer readable medium configured for accepting first values of the plurality of properties, and for using or setting an initial criterion for determining an access disconnection, and for accepting second values of the plurality of properties and for adjusting the criterion based on the second values.

10. The system according to claim 9, further comprising a lookup table in the computer or in the memory, the lookup table including a table of minimum and maximum impedance values for the plurality of properties concerning the patient and the extracorporeal blood therapy machine.

11. The system according to claim 9 wherein the contacts comprise connectors configured for connecting to arterial and venous access needles.

12. The system according to claim 9, wherein the extracorporeal therapy machine comprises a hemodialysis machine, and further comprising the hemodialysis machine.

13. The system according to claim 9, wherein the plurality of properties concerning the patient and the extracorporeal blood therapy machine are further selected from the group consisting of a value of a component of blood chemistry, an impedance, a capacitance, and a resistance.

14. The system according to claim 9, further comprising at least one input device and at least one output device operably connected to the computer.

15. The system according to claim 9, wherein the electrical circuit further comprises a current or voltage source connected to the contacts.

16. The system according to claim 9, wherein the at least one electrical property is selected from the group consisting of an impedance, a resistance, a conductivity, and a capacitance.

17. An extracorporeal therapy machine, comprising:
a machine for administering a dialysis therapy;
arterial and venous contacts configured for use with the machine;
an electrical circuit connected to the contacts, the electrical circuit configured for sensing an electrical property concerning the patient or a component of the machine;
at least one sensor configured for sensing at least one of a plurality of properties concerning the patient, the therapy, and the machine, the at least one sensor selected from the group consisting of a clock, a pressure sensor, a temperature sensor, and a speed sensor;
a computer having a memory, the computer configured for receiving and storing values for the plurality of properties concerning the patient, the therapy, and the machine;
a computer program on a computer readable medium configured for accepting first values of the plurality of properties sensed by the at least one sensor, and for setting an initial criterion for determining an access disconnection, and for accepting second values of the plurality of properties sensed by the at least one sensor and for adjusting the criterion based on the second values; and
at least one input device and one output device operably connected to the computer.

18. The extracorporeal therapy machine according to claim 17, further comprising a pump, wherein the speed sensor includes an encoder on the actuator of the pump.

19. The extracorporeal therapy machine of claim 17, wherein the electrical circuit is selected from the group consisting of a current source and a voltage source.

20. A hemodialysis machine for administering a hemodialysis therapy, the machine comprising:
a housing containing components of the machine;
a monitor for monitoring the machine;
a dialyzer;
at least one blood pump for moving blood of the patient to and from the patient and through the dialyzer;
arterial and venous contacts configured for use with the machine;
an electrical circuit connected to the contacts, the electrical circuit configured for sensing an electrical property concerning the patient or a component of the machine;
a computer having a memory, the computer configured for controlling the machine and for receiving and storing values of a plurality of properties concerning the patient, the therapy, and the machine, the plurality of properties selected from the group consisting of a distance between access needles for the hemodialysis therapy, an elapsed time of the therapy, a temperature of at least a portion of the machine, a speed of a pump of the blood pump of the machine, administration of a bolus, and a dialysate temperature;
a computer program on a computer readable medium configured for accepting first values of the plurality of properties, and for setting an initial value for a criterion for determining an access disconnection, and for accepting second values of the plurality of properties and adjusting the criterion value based on the second values; and
at least one input device and one output device operably connected to the computer.

21. The machine of claim 20, wherein the contacts comprise arterial and venous access needles.

22. The machine of claim 20, wherein the criterion is a minimum or a maximum value of an impedance, a resistance, a conductivity, or a capacitance.

23. The machine of claim 20, wherein the computer program includes instructions for narrowing a range of minimum and maximum values of the criterion.

* * * * *